(12) United States Patent
Ferree

(10) Patent No.: US 7,201,774 B2
(45) Date of Patent: Apr. 10, 2007

(54) ARTIFICIAL INTERVERTEBRAL DISC REPLACEMENTS INCORPORATING REINFORCED WALL SECTIONS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 101 days.

(21) Appl. No.: 10/407,554

(22) Filed: Apr. 4, 2003

(65) Prior Publication Data

US 2003/0191536 A1    Oct. 9, 2003

Related U.S. Application Data

(63) Continuation-in-part of application No. 10/303,385, filed on Nov. 25, 2002, which is a continuation-in-part of application No. 10/191,639, filed on Jul. 9, 2002, which is a continuation-in-part of application No. 09/415,382, filed on Oct. 8, 1999, now Pat. No. 6,419,704.

(51) Int. Cl.
*A61F 2/06* (2006.01)

(52) U.S. Cl. ................. 623/17.11; 623/17.12

(58) Field of Classification Search .. 623/17.11–17.16, 623/23.41, 23.5, 23.51
See application file for complete search history.

(56) References Cited

U.S. PATENT DOCUMENTS

| | | | |
|---|---|---|---|
| 2,677,369 A | 5/1954 | Knowles | 128/92 |
| 3,366,975 A | 2/1968 | Pangman | 3/36 |
| 3,426,364 A | 2/1969 | Lumb | 3/1 |
| 3,551,560 A | 12/1970 | Thiele | 424/95 |
| 3,593,342 A | 7/1971 | Niebauer | 3/1 |
| 3,648,294 A | 3/1972 | Shahrestani | 3/1 |
| 3,855,638 A | 12/1974 | Pilliar | 3/1 |
| 3,867,728 A | 2/1975 | Stubstad et al. | 3/1 |
| 3,875,595 A | 4/1975 | Froning | 3/1 |
| 3,883,902 A | 5/1975 | Lynch | 3/36 |
| 4,229,839 A | 10/1980 | Schwemmer | 3/1.91 |
| 4,309,777 A | 1/1982 | Patil | 3/1.91 |
| 4,349,921 A | 9/1982 | Kuntz | 3/1 |
| 4,657,550 A | 4/1987 | Daher | 606/61 |
| 4,663,358 A | 5/1987 | Hyon et al. | 521/64 |
| 4,707,872 A | 11/1987 | Hessel | 5/451 |
| 4,714,469 A | 12/1987 | Kenna | 623/17 |
| 4,759,766 A | 7/1988 | Buettner-Janz et al. | 623/17 |
| 4,772,287 A * | 9/1988 | Ray et al. | 623/17.12 |
| 4,863,477 A | 9/1989 | Monson | 623/17.11 |
| 4,874,389 A | 10/1989 | Downey | 623/17 |
| 4,878,915 A | 11/1989 | Brantigan | 623/17 |
| 4,904,260 A | 2/1990 | Ray et al. | 623/17.16 |
| 4,911,718 A | 3/1990 | Lee et al. | 623/17 |
| 4,917,704 A | 4/1990 | Frey et al. | 623/17 |

(Continued)

*Primary Examiner*—Suzette Gherbi
(74) *Attorney, Agent, or Firm*—Gifford, Krass, Groh, Sprinkle, Anderson & Citkowski, PC

(57) ABSTRACT

An Artificial Disc Replacement (ADR) includes a body and/or outer wall that is fortified, reinforced, stiffened or otherwise strengthened with a higher durometer, for example, where it rests against a weakened or deficient area of the annulus fibrosis (AF). The "less stiff" portions facilitate the transfer of load to the healthier portion of the AF. A hydrogel or other compressible and/or resilient material may be used within the center of the ADR to selectively transfer the forces to the outer wall. The outer wall may constructed of an elastomer, and may include a radial ply, bias ply, and/or belted construction. Methods of determining a properly sized ADR are also disclosed.

17 Claims, 3 Drawing Sheets

U.S. PATENT DOCUMENTS

| | | | |
|---|---|---|---|
| 4,932,969 A | 6/1990 | Frey et al. | 623/17 |
| 4,946,378 A | 8/1990 | Hirayama et al. | 623/17 |
| 5,002,576 A | 3/1991 | Furhmann et al. | 623/17 |
| 5,015,247 A | 5/1991 | Michelson | 606/61 |
| 5,026,373 A | 6/1991 | Ray et al. | 606/61 |
| 5,035,716 A | 7/1991 | Downey | 623/17 |
| 5,047,055 A * | 9/1991 | Bao et al. | 623/17.16 |
| 5,071,437 A | 12/1991 | Steffee | 623/17 |
| 5,108,438 A | 4/1992 | Stone | 623/17 |
| 5,123,926 A | 6/1992 | Pisharodi | 623/17 |
| 5,171,280 A | 12/1992 | Baumgartner | 623/17 |
| 5,171,281 A | 12/1992 | Parsons et al. | 623/17 |
| 5,192,326 A * | 3/1993 | Bao et al. | 623/17.16 |
| 5,192,327 A | 3/1993 | Brantigan | 606/60 |
| 5,246,458 A | 9/1993 | Graham | 623/17 |
| 5,258,031 A | 11/1993 | Salib et al. | 623/17 |
| 5,258,043 A | 11/1993 | Stone | 623/66 |
| 5,292,332 A | 3/1994 | Lee | 606/213 |
| 5,314,477 A | 5/1994 | Marnay | 623/17 |
| 5,320,644 A | 6/1994 | Baumgartner | 623/17 |
| 5,336,223 A | 8/1994 | Rogers | 606/61 |
| 5,344,459 A * | 9/1994 | Swartz | 623/14.12 |
| 5,370,697 A | 12/1994 | Baumgartner | 623/17 |
| 5,375,823 A | 12/1994 | Navas | 267/195 |
| 5,401,269 A | 3/1995 | Buttner-Janz et al. | 623/17 |
| 5,425,773 A | 6/1995 | Boyd et al. | 623/17 |
| 5,458,642 A | 10/1995 | Beer | 623/17 |
| 5,464,421 A | 11/1995 | Wortrich | 606/213 |
| 5,514,180 A | 5/1996 | Heggeness et al. | 623/17.11 |
| 5,534,028 A * | 7/1996 | Bao et al. | 623/17.16 |
| 5,534,030 A | 7/1996 | Navarro et al. | 623/17 |
| 5,545,229 A | 8/1996 | Parsons et al. | 623/17 |
| 5,556,431 A | 9/1996 | Buttner-Jan | 623/17 |
| 5,571,192 A | 11/1996 | Schonhoffer | 606/61 |
| 5,609,635 A | 3/1997 | Michelson | 623/17 |
| 5,645,565 A | 7/1997 | Rudd et al. | 606/213 |
| 5,645,596 A | 7/1997 | Kim et al. | 623/17 |
| 5,645,597 A | 7/1997 | Krapiva | 623/17 |
| 5,674,294 A | 10/1997 | Bainville et al. | 623/17 |
| 5,674,296 A | 10/1997 | Bryan et al. | 623/17 |
| 5,683,465 A | 11/1997 | Shinn et al. | 623/17 |
| 5,693,100 A | 12/1997 | Pisharodi | 623/17.16 |
| 5,702,450 A | 12/1997 | Bisserie | 623/17 |
| 5,702,455 A | 12/1997 | Saggar | 623/17.15 |
| 5,711,960 A | 1/1998 | Shikinami | 424/426 |
| 5,716,416 A | 2/1998 | Lin | 623/17 |
| 5,800,549 A | 9/1998 | Bao et al. | 623/17 |
| 5,814,084 A | 9/1998 | Grivas et al. | 623/23.48 |
| 5,824,093 A | 10/1998 | Ray et al. | 623/17 |
| 5,824,094 A | 10/1998 | Serhan et al. | 623/17 |
| 5,865,845 A | 2/1999 | Thalgott | 623/17 |
| 5,865,846 A | 2/1999 | Bryan et al. | 623/17 |
| 5,888,226 A | 3/1999 | Rogozinski | 623/17 |
| 5,893,889 A | 4/1999 | Harrington | 623/17 |
| 5,899,941 A | 5/1999 | Nishijima et al. | 623/17 |
| 5,906,616 A | 5/1999 | Pavlov et al. | 606/61 |
| 5,928,284 A | 7/1999 | Mehdizadeh | 623/17 |
| 5,964,807 A | 10/1999 | Gan et al. | 623/17.11 |
| 5,976,186 A | 11/1999 | Bao et al. | 623/17.16 |
| 6,022,376 A | 2/2000 | Assell et al. | 623/17.16 |
| 6,045,554 A | 4/2000 | Grooms et al. | 606/73 |
| 6,090,112 A | 7/2000 | Zucherman et al. | 606/61 |
| 6,110,210 A | 8/2000 | Norton et al. | 623/17.16 |
| 6,113,639 A | 9/2000 | Ray et al. | 623/17.16 |
| 6,132,465 A * | 10/2000 | Ray et al. | 623/17.16 |
| 6,146,420 A | 11/2000 | McKay | 623/17.11 |
| 6,187,048 B1 | 2/2001 | Milner et al. | 623/17.12 |
| 6,200,347 B1 | 3/2001 | Anderson et al. | 623/11.11 |
| 6,214,050 B1 | 4/2001 | Huene | 623/17.15 |
| 6,245,072 B1 | 6/2001 | Zdeblick et al. | 606/61 |
| 6,261,586 B1 | 7/2001 | McKay | 424/422 |
| 6,264,695 B1 * | 7/2001 | Stoy | 623/17.16 |
| 6,270,528 B1 | 8/2001 | McKay | 623/16.11 |
| 6,306,177 B1 * | 10/2001 | Felt et al. | 623/23.6 |
| 6,533,818 B1 * | 3/2003 | Weber et al. | 623/17.16 |
| 6,786,930 B2 * | 9/2004 | Biscup | 623/16.11 |
| 2001/0020186 A1 | 9/2001 | Boyce et al. | 623/17.16 |
| 2001/0034553 A1 | 10/2001 | Michelson | 623/17.11 |
| 2001/0039458 A1 | 11/2001 | Boyer, II et al. | 623/23.63 |
| 2001/0056302 A1 | 12/2001 | Boyer, II et al. | 623/17.15 |
| 2002/0077701 A1 * | 6/2002 | Kuslich | 623/17.12 |
| 2003/0125807 A1 * | 7/2003 | Lambrecht et al. | 623/17.16 |
| 2003/0199984 A1 * | 10/2003 | Trieu | 623/17.16 |

* cited by examiner

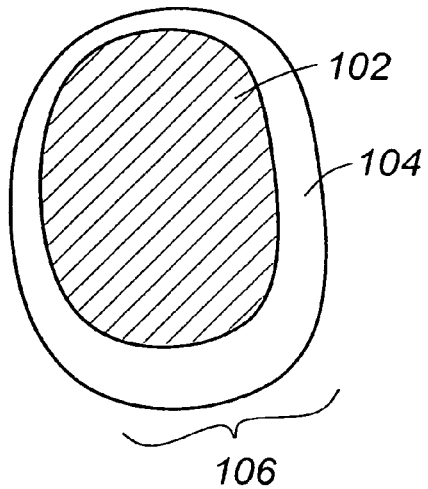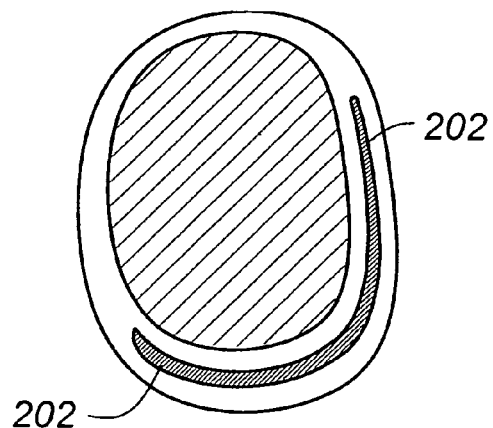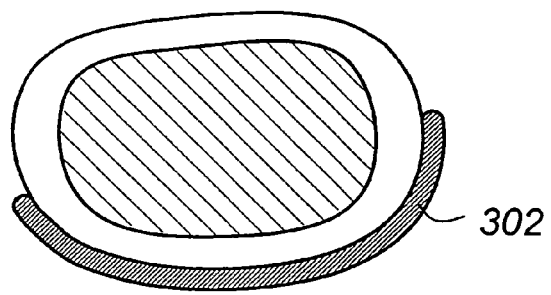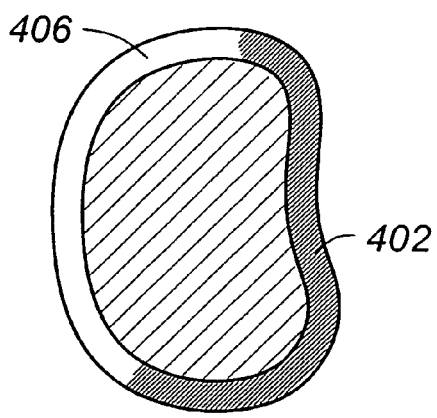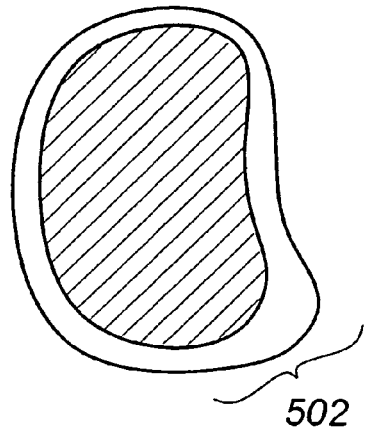
Fig - 1
Fig - 2
Fig - 3
Fig - 4
Fig - 5

ARTIFICIAL INTERVERTEBRAL DISC REPLACEMENTS INCORPORATING REINFORCED WALL SECTIONS

REFERENCE TO RELATED APPLICATIONS

This application is a continuation-in-part of U.S. patent application Ser. No. 10/303,385, filed Nov. 25, 2002; which is a continuation-in-part of U.S. patent application Ser. No. 10/191,639, filed Jul. 9, 2002 and Ser. No. 09/415,382, filed Oct. 8, 1999, now U.S. Pat. No. 6,419,704. The entire content of each application and patent is incorporated herein by reference.

FIELD OF THE INVENTION

This invention relates generally to surgical techniques and prosthetic components therefore and, in particular, to intervertebral disc replacement apparatus and methods of implanting the same.

BACKGROUND OF THE INVENTION

Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

The spine supports the body, and protects the spinal cord and nerves. The vertebrae of the spine are also supported by ligaments, tendons, and muscles which allow movement (flexion, extension, lateral bending, and rotation). Motion between vertebrae occurs through the disc and two facet joints. The disc lies in the front or anterior portion of the spine. The facet joints lie laterally on either side of the posterior portion of the spine.

The human intervertebral disc is an oval to kidney bean shaped structure of variable size depending on the location in the spine. The outer portion of the disc is known as the annulus fibrosus. The annulus is formed of 10 to 60 fibrous bands. The fibers in the bands alternate their direction of orientation by 30 degrees between each band. The orientation serves to control vertebral motion (one half of the bands tighten to check motion when the vertebra above or below the disc are turned in either direction).

The annulus contains the nucleus pulposus which serves to transmit and dampen axial loads. A high water content (70–80 percent) assists the nucleus in this function. The water content has a diurnal variation. The nucleus imbibes water while a person lies recumbent. Activity squeezes fluid from the disc. Nuclear material removed from the body and placed into water will imbibe water swelling to several times its normal size. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per micro liter.

Interestingly, the adult disc is the largest avascular structure in the human body. Given the lack of vascularity, the nucleus is not exposed to the body's immune system. Most cells in the nucleus obtain their nutrition and fluid exchange through diffusion from small blood vessels in adjacent vertebra.

The disc changes with aging. As a person ages the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised.

The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments of disc degeneration are destructive. One group of procedures removes the nucleus or a portion of the nucleus; lumbar discectomy falls in this category. A second group of procedures destroy nuclear material; Chymopapin (an enzyme) injection, laser discectomy, and thermal therapy (heat treatment to denature proteins) fall in this category.

A third group, spinal fusion procedures either remove the disc or the disc's function by connecting two or more vertebra together with bone. These destructive procedures lead to acceleration of disc degeneration. The first two groups of procedures compromise the treated disc. Fusion procedures transmit additional stress to the adjacent discs. The additional stress results in premature disc degeneration of the adjacent discs.

Prosthetic disc replacement offers many advantages. The prosthetic disc attempts to eliminate a patient's pain while preserving the disc's function. Current prosthetic disc implants, however, either replace the nucleus or the nucleus and the annulus. Both types of current procedures remove the degenerated disc component to allow room for the prosthetic component. Although the use of resilient materials has been proposed, the need remains for further improvements in the way in which prosthetic components are incorporated into the disc space, and in materials to ensure strength and longevity. Such improvements are necessary, since the prosthesis may be subjected to 100,000,000 compression cycles over the life of the implant.

SUMMARY OF THE INVENTION

U.S. Pat. No. 6,419,704 discloses artificial replacements for natural intervertebral discs in humans and animals. Broadly, a shaped body assumes a final volume sized to consume at least a portion of the intervertebral disc space, and a material associated with the shaped body enabling the body to cyclically compress and expand in a manner similar to the disc material being replaced. The body may be composed of a compressible material, such as polymeric urethane, hydrogel, or other suitable elastomers, or may include a filling to impart an appropriate level of compressibility. The superior and inferior surfaces may be convex, and may further include grooves, spikes, or other protrusions to maintain the body within the intervertebral space. The body may further be wedge-shaped to help restore or maintain lordosis, particularly if the prosthesis is introduced into the cervical or lumbar regions of the spine.

To enhance strength or longevity, the body may further include the use of fiber-reinforced materials on one or more outer surfaces or wall structures, as the case may be. Similar to commercial tire construction, such fiber-reinforced materials may be of a bias-ply, radial-ply or bias-belted construction. One configuration include an outer compressible member peripherally attached to a central "hub," similar, at least in concept, to the which a tire is mounted onto a wheel.

The instant invention extends the teachings of the '704 patent by providing an Artificial Disc Replacement (ADR) that is structurally and functionally more like a natural disc. A natural disc converts axial load from the nucleus pulposus (NP) to radial hoop stress on the annulus fibrosus (AF), and the invention recognizes that generally the anterior portion of a natural annulus fibrosus (AF) is thicker. Resultantly, the posterior and posterior-lateral portion of the AF is thinner and often torn. Furthermore, the posterior portion of the AF has more pain fibers.

The preferred embodiments accordingly dispense with a central hub, and the "belt" is limited to a portion of the outer wall of the body. The body of the device and/or a portion of the outer wall is fortified, reinforced, stiffened or otherwise strengthened with a higher durometer, for example, where it rests against a weakened or deficient area of the annulus fibrosus (AF). The "less stiff" portions facilitate the transfer of load to the healthier portion of the AF.

A hydrogel or other compressible and/or resilient material may be used within the center of the ADR to selectively transfer the forces to the outer wall. As described in U.S. Pat. No. 6,419,704, the outer wall may constructed of an elastomer, and may include a radial ply, bias ply, and/or belted construction. Methods of determining a properly sized ADR are also disclosed.

The ADR is preferably inserted into the disc space from a lateral approach as described in my co-pending patent application Ser. No. 10/438,605. An osteotomy of the vertebrae as described in my co-pending patent application Ser. No. 10/421,434 may also be beneficial.

BRIEF DESCRIPTION OF THE DRAWINGS

FIG. 1 is an axial cross section through an ADR constructed in accordance with this invention;

FIG. 2 is an axial cross section through another embodiment of an ADR according to this invention;

FIG. 3 is an axial cross section through an alternative ADR embodiment;

FIG. 4 is an axial cross section through a further alternative ADR embodiment;

FIG. 5 is an axial cross section of an alternative embodiment of the ADR of FIG. 1;

DETAILED DESCRIPTION OF THE INVENTION

Figure 6:
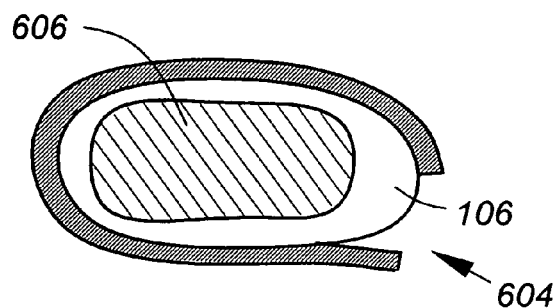
FIG. 6 is an axial cross section of a disc and the embodiment of the ADR of FIG. 1.

Turning now to the various drawings, FIG. 1 is an axial cross section through an ADR constructed in accordance with this invention. Area 102 represents a compressible or resilient cushioning material, such as, hydrogel, polyurethane, or other polymer, including elastomers. The outer wall 104 of the ADR includes one or more areas with increased radial stiffness. For example, note that the portion 106 of the wall in this case is intentionally thickened to increase the radial stiffness of that portion.

In addition to thickening a portion of the wall, a different material may be used, provided either through bonding or through a change in composition. Alternatively, a material may be used that is strengthened, fortified, reinforced or otherwise stiffened through the application of energy or a chemical. For example, ultraviolet light or another form of radiation may be used to locally stiffen a section of the wall, as would be the case with certain types of polymerization techniques. Or a chemical may be injected into the wall causing a change in durometer. An advantage of these alternative techniques is that the stiffening may be carried out with the ADR in situ, perhaps through the very defect in the annulus fibrosis (AF) to be fortified.

FIG. 2 is an axial cross section through another embodiment of an ADR according to this invention. In this case, a portion of the wall contains a material 202 with increased durometer.

FIG. 3 is an axial cross section through an alternative ADR embodiment. The material 302 with increased radial stiffness is placed over a portion of the wall. The stiffer material can be adhered to the wall or compositionally transition. FIG. 4 is an axial cross section through a further alternative ADR embodiment, wherein the wall composite of a material or materials with varying durometers. For example, portion 402 may be stiffer in a radial direction than portion 406.

FIG. 5 is an axial cross section of an alternative embodiment of the ADR drawn in FIG. 1. A more focal area 502 of the outer wall is thicker to better fit into a hole in the AF.

FIG. 6 is an axial cross section of a disc and the embodiment of the ADR drawn in FIG. 1. In this case, the thicker portion 106 of the ADR is aligned with a defect 604 in the AF. Axial loads to the center 606 are again transferred to the outer wall of the body, which selectively applies hoop stress to the intact area of the AF. The ADR may be inserted through the defect in the AF.

Figure 7:
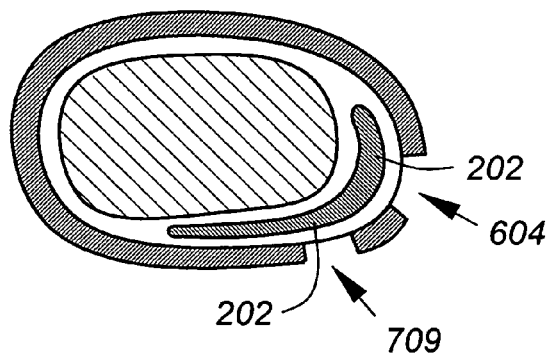
FIG. 7 is an axial cross section of a disc and the embodiment of the ADR of FIG. 2.

FIG. 7 is an axial cross section of a disc and the embodiment of the ADR drawn in FIG. 2. The stiffer portion 202 is aligned with two deficient areas 708, 709 of the AF. Either or both of the defects may be surgically created or may represent deficient areas in the AF from a herniated Nucleus Pulposus.

Figure 8:
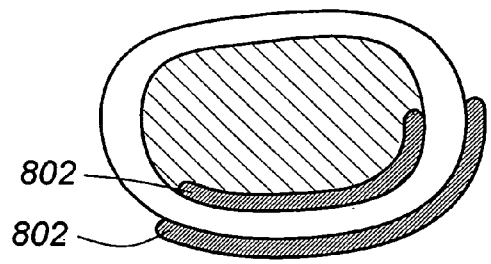
FIG. 8 is an axial cross section through an alternative embodiment of an ADR incorporating a sleeve with increased radial stiffness surrounds a portion of the implantable body.

FIG. 8 is an axial cross section through an alternative embodiment of the ADR, wherein a sleeve 802 with increased radial stiffness surrounds a portion of the wall.

Figure 9:
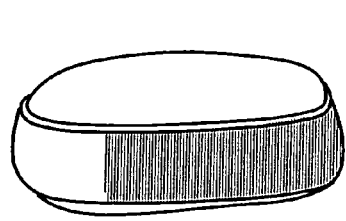
FIG. 9 is an oblique view of the embodiment of the ADR drawn in FIG. 3 or FIG. 8.
Figure 10:
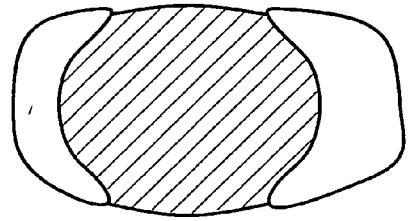
FIG. 10 is a sagittal cross section of the embodiment of the ADR drawn in FIG. 1 or FIG. 5.
Figure 11:
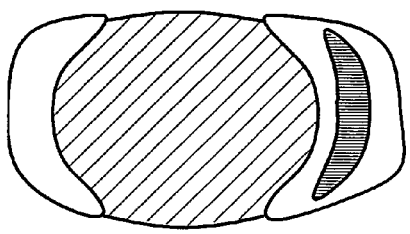
FIG. 11 is a sagittal cross section of the embodiment of the ADR drawn in FIG. 2.

FIG. 9 is an oblique view of the embodiment of the ADR drawn in FIG. 3 or FIG. 8. Note that the superior and inferior portions of the ADR are free to articulate against the vertebral endplates. FIG. 10 is a sagittal cross section of the embodiment of the ADR drawn in FIG. 1 or FIG. 5. FIG. 11 is a sagittal cross section of the embodiment of the ADR drawn in FIG. 2.

Figure 12:
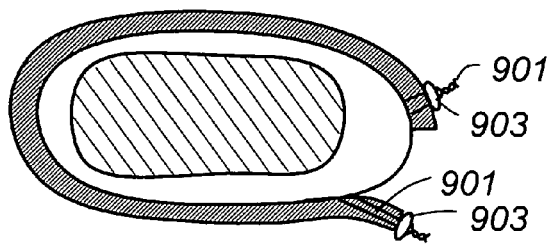
FIG. 12 is an axial cross section of a disc and the embodiment of the ADR drawn in FIG. 1.

FIG. 12 is an axial cross section of a disc and the embodiment of the ADR drawn in FIG. 1, but wherein the ADR is attached or adhered to the AF. The drawing illustrates the use of sutures 901 passed from the ADR, through the AF. The sutures can be tied over a button 903 or other device over the AF.

Figure 13:
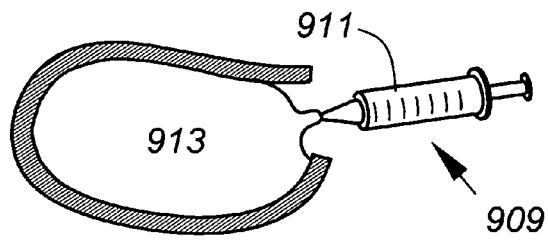
FIG. 13 is an axial cross section of a disc and a device to measure the size of an ADR needed.

FIG. 13 is an axial cross section of a disc and a device 909 according to a different aspect of the invention used to measure the size of a needed ADR. An air or liquid filled syringe 911 is attached to an inflatable balloon 913 within the AF. The measuring the volume of air or liquid needed to fill the balloon helps the surgeon select the right size ADR.

Figure 14:
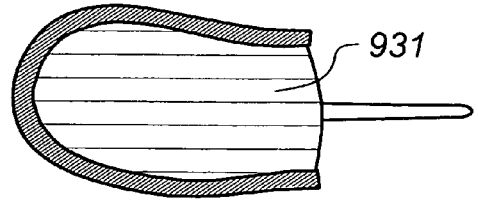
FIG. 14 is an axial cross section through a disc and an alternative measurement device.

FIG. 14 is an axial cross section through a disc and an alternative measurement device according to the invention. In this case an 931 in-situ curing polymer is placed into the disc space. The mold of the disc space is created by curing of the polymer. The mold can be removed by a handle within the polymer. The mold helps the surgeon select ADR size and shape.

Figure 15:
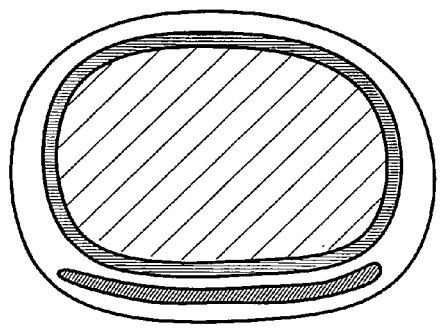
FIG. 15 is an axial cross section of yet a different embodiment of an ADR according to the invention.

FIG. 15 is an axial cross section of another embodiment of the ADR including an outer wall with two layers that may be bonded to one another or materially transition. Alternatively, movement may be allowed between the layers of the outer wall. As with the embodiment of the ADR drawn in FIG. 2, the outer layer exhibits an area with increased radial stiffness.

I claim:

1. An artificial disc replacement (ADR) configured for placement within an annulus fibrosis (AF) having a defective or weakened section, the ADR comprising:
   a cushioning material having a top surface, a bottom surface, and an outer sidewall;
   a band of material other than the cushioning material completely encircling the outer sidewall; and
   wherein only a portion of the band of material is locally fortified so that stresses applied to the top and bottom surfaces result in less pressure on the defective or weakened section as compared to other sections of the AF.

2. The ADR of claim 1, wherein the local fortification is achieved through a localized thickening of the band of material.

3. The ADR of claim 1, wherein the local fortification is achieved through the use of a composite band incorporating a second, stiffer material.

4. The ADR of claim 3, wherein the second material is bonded to, or embedded within the band.

5. The ADR of claim 3, wherein the second material compositionally transitions to and from the band of material.

6. The ADR of claim 1, wherein the band of material includes a bias-ply, radial, or bias-belted fiber-reinforced structure.

7. The ADR of claim 6, wherein the fiber-reinforced wall structure includes one or more biologically compatible fabrics composed of nylon, polyester, metal, fiberglass, or a combination thereof.

8. The ADR of claim 1, wherein the cushioning material is a gas, liquid or gel to promote resilient compressibility.

9. The ADR of claim 1, wherein the cushioning material is a hydrogel.

10. The ADR of claim 1, wherein the local fortification is associated with the posterior section.

11. The ADR of claim 1, wherein the local fortification is associated with the posterior, lateral or both the posterior and lateral sections.

12. A method of replacing at least a portion of a natural intervertebral disc within an annulus fibrosis (AF) having a defective or weakened section, comprising the steps of:
   providing an artificial disc replacement (ADR) having a compressible center portion entirely surrounded by a band of material, only a section of which is asymmetrically fortified to withstand greater stress transferred from the center portion during compression; and
   implanting the ADR within a disc space such that the fortified section is aligned with the defective or weakened section of the AF.

13. The method of claim 12, wherein the local fortification is associated with the posterior section.

14. The method of claim 12, wherein the local fortification is associated with the posterior, lateral or both the posterior and lateral sections.

15. A method of determining the proper size for an artificial disc replacement (ADR), comprising the steps of:
   filling a disc space with a measured volume of gas or liquid; and
   selecting an ADR in accordance with the measured volume.

16. The method of claim 15, wherein the volume is measured using a graduated syringe coupled to an inflatable balloon within the disc space.

17. The method of claim 15, wherein the liquid is a polymer or other substance which is cured within the disc space, removed and measured to determine the volume.

* * * * *